United States Patent [19]

Brite

[11] 4,299,258

[45] Nov. 10, 1981

[54] METHOD OF INSECTICIDE APPLICATION

[76] Inventor: Alan D. Brite, 5147 W. Jefferson Blvd., Los Angeles, Calif. 90061

[21] Appl. No.: 53,986

[22] Filed: Jul. 2, 1979

[51] Int. Cl.³ .............................................. B65B 1/16
[52] U.S. Cl. ........................................ 141/1; 141/26; 222/1; 401/185
[58] Field of Search ............................ 141/2, 18-27, 141/98, 1, 392; 222/1; 401/183, 185; 424/148

[56] References Cited

U.S. PATENT DOCUMENTS 2,058,118  10/1936  White ................................. 141/392
2,243,451  5/1941  Bauer ................................. 141/392
2,489,035  11/1949  Jones ................................. 141/26

FOREIGN PATENT DOCUMENTS 12806 of 1911 United Kingdom ............... 141/392

Primary Examiner—Houston S. Bell, Jr.
Attorney, Agent, or Firm—Lyon & Lyon

[57] ABSTRACT

A method of applying an insecticide, the insecticide containing a mixture of powdered boric acid, denatonium benzoate or sucrose octa-acetate, magnesium stearate, silica gel or triacalcium phosphate and a non-white powdered pigment.

4 Claims, 4 Drawing Figures

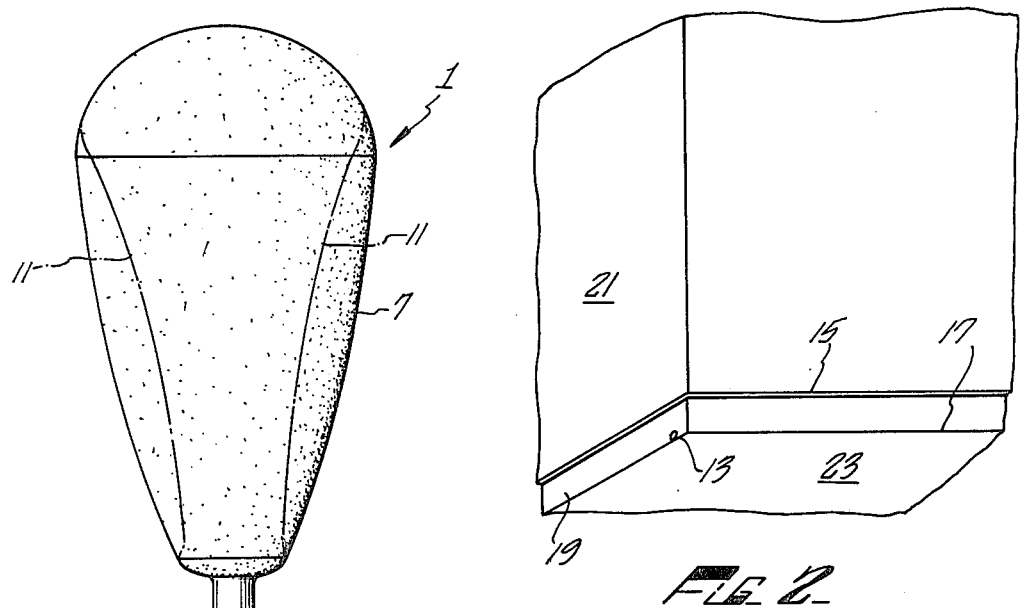
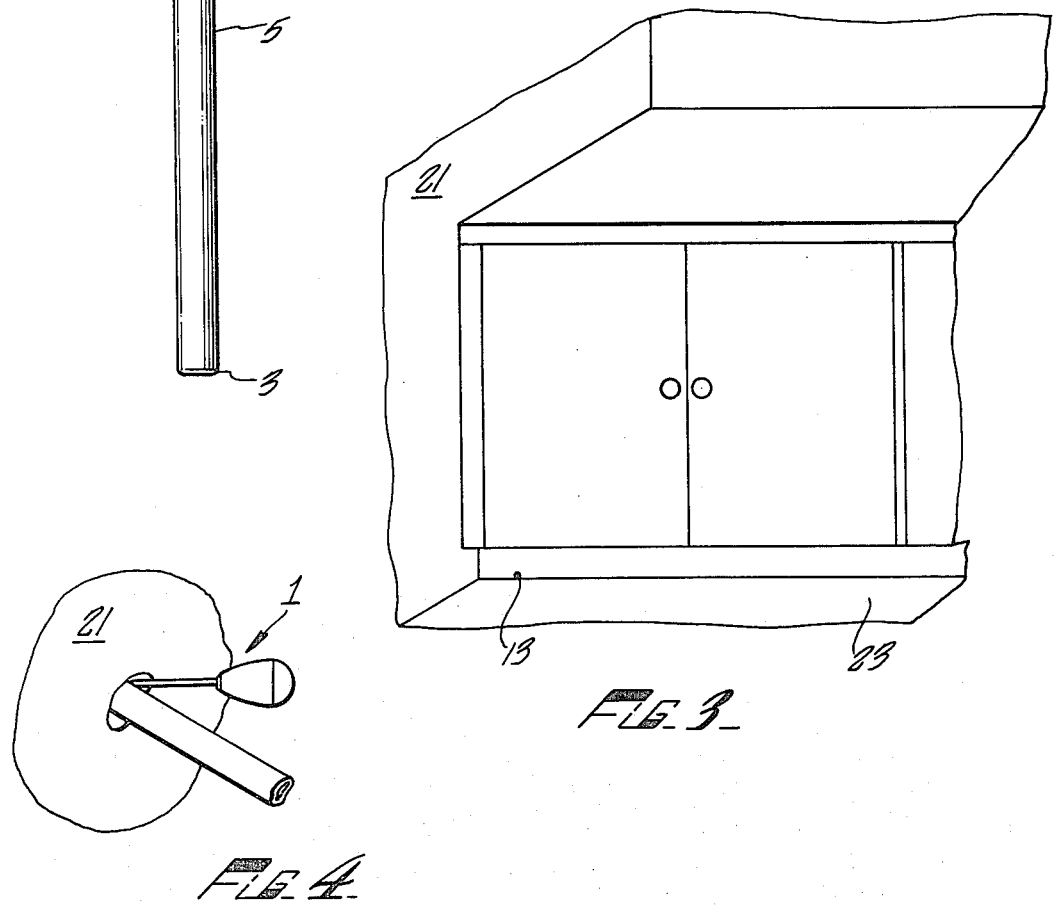

METHOD OF INSECTICIDE APPLICATION

The instant invention is directed to a method of insecticide application.

FIG. 1 is a pictorial view of a pipette utilized in practicing the method of this invention.

FIG. 2 is a partial sectional view illustrating the method of this invention.

FIGS. 3 and 4 are pictorial views showing an aperture created in a junction of erected construction material and the use of a pipette in practicing the method of this invention.

This invention is directed to a method of application of an insecticide, the insecticide comprising a mixture of powdered boric acid, sucrose octa-acetate or denatonium benzoate, and magnesium stearate, silica gel or tricalcium phosphate, and a non-white pigment. Preferably, the boric acid is defined as having a particle size of approximately 100 to 400 mesh.

In a preferred embodiment the insecticide contains a mixture of at least 95% by weight boric acid; a member selected from the group of silica gel, tricalcium phosphate and magnesium stearate in a concentration of less than 5% by weight; a member selected from the group of denatonium benzoate and sucrose octa-acetate; and powdered blue pigment each in a concentration of less than 1% by weight.

It has been found that the insecticide above described may be applied by means of a pipette which fluidizes the otherwise solid insecticide, because the mixture does not have an appreciable affinity for water and is of an appropriate density and particle size sufficient for such application. This composition is more fully disclosed and described in my pending U.S. Patent Application titled "Insecticide" filed Mar. 29, 1979 hereby incorporated by reference.

Referring now to FIG. 1, the method of insecticide application of this invention will be more completely described.

FIG. 1 illustrates a pipette 1, having a tip portion 3, a stem portion 5 and a resilient bulbous portion 7. When it is desired to apply the insecticide of this invention, at least the tip portion 3 of the pipette 1 is inserted into a container (not shown) of the insecticide and the resilient portion 7 is at least partially collapsed through the configuration shown by dotted lines 11 by means of an external force. Upon release of the external force, the resilient bulbous portion 7 seeks to reassume the configuration shown by the solid lines defining the resilient portion 7 and the suction therein created draws insecticide 9 into at least the tip and stem portions, 3 and 5 respectively, of the pipette 1.

Next, at least the tip portion 3 of the pipette 1 is inserted into an aperture 13 created in a junction 17 of erected construction material such as molding 19 of wall 21 and floor 23. Alternately, the apertures 13 may be formed at the juncture 15 of molding 19. It has been determined that the insects for which the insecticide is particularly utilitarious, namely cockroaches, tend to travel along junctions within buildings and accordingly it has thus been determined that this is the best place to place an aperture for the application of the insecticide.

Having described this invention in detail, it is understood that modifications obvious to those skilled in the art may be made without departing from the concept of this invention and accordingly the invention is to be limited only by the appended claims attached hereto.

I claim:

1. A method of solid insecticide application comprising:
    inserting at least the tip portion of a pipette into a container of insecticide containing a powdered mixture of powdered boric acid, denatonium benzoate, magnesium stearate and a non-white powdered pigment;
    collapsing, at least partially, by means of external pressure a resilient bulbous portion of said pipette, and then releasing said external pressure thereby allowing for the opening of said bulbous portion to its initial size thereby;
    drawing said solid insecticide into at least the tip and stem portions of said pipette;
    inserting said tip portion into an aperture located along a junction of erected construction material; and
    collapsing, at least partially, by means of external pressure, said resilient bulbous portion of said pipette and thereby;
    forcing said solid insecticide into and through said aperture.

2. The method of insecticide application claimed in claim 1 wherein said method further includes:
    forming at least one aperture located along a junction of erected construction materials.

3. The method of insecticide application claimed in claim 1 wherein the boric acid is further defined as having a particle size of approximately 100 to 400 mesh.

4. The method of solid insecticide application claimed in claim 1 wherein said insecticide is further defined as comprising a powdered mixture of at least 95% by weight powdered boric acid, a member selected from the group comprising silica gel, tricalcium phosphate and magnesium stearate in a concentration of less than 5% by weight and a member selected from the group comprising denatonium benzoate and sucrose octa-acetate, and powdered blue pigment, each being in a concentration of less than 1% by weight.

* * * * *